United States Patent [19]
Brown

[11] Patent Number: 5,350,376
[45] Date of Patent: Sep. 27, 1994

[54] OPTICAL CONTROLLER DEVICE

[75] Inventor: Joseph D. Brown, Acworth, Ga.

[73] Assignee: CeramOptec, Inc., Enfield, Conn.

[21] Appl. No.: 47,190

[22] Filed: Apr. 16, 1993

[51] Int. Cl.$^5$ .............................................. A61B 17/36
[52] U.S. Cl. ...................................... 606/12; 606/10; 607/89; 128/898
[58] Field of Search ............................ 606/10-17; 128/395-398, 898; 607/88, 89

[56] References Cited

U.S. PATENT DOCUMENTS

| | | | |
|---|---|---|---|
| 3,487,835 | 1/1970 | Koester et al. | |
| 3,865,113 | 2/1975 | Sharon et al. | |
| 4,316,467 | 2/1982 | Muckerheide | 606/12 |
| 4,994,059 | 2/1991 | Kosa et al. | 606/12 |
| 5,071,417 | 12/1991 | Sinofsky | 606/10 |
| 5,098,427 | 3/1992 | Hessel et al. | 606/11 |

FOREIGN PATENT DOCUMENTS 75912 4/1983 European Pat. Off. .
3105297 12/1981 Fed. Rep. of Germany .

*Primary Examiner*—Stephen C. Pellegrino
*Assistant Examiner*—Michael Peffley
*Attorney, Agent, or Firm*—Kenneth P. Glynn

[57] ABSTRACT

An improved configuration for a surgical laser instrument to provide the alternate contact cutting and no-contact coagulating of biological tissues by means of a fiber-optically guided irradiation of a laser is disclosed. This configuration includes instrumentation to enable discrimination between background illumination (i.e. xenon illumination scopes, room lights) and white light produced by the burning of tissue residue at the distal fiber tip. White light is described as a light having a wavelength between 0.3 to 0.9 mm. This improvement has the advantages of preventing background illumination from interfering with operation of a laser equipped with a white light feedback control device. Ultimately, this provides the surgeon with a more predictable laser delivery device which subsequently makes the laser safer to use.

4 Claims, 3 Drawing Sheets

OPTICAL CONTROLLER DEVICE

BACKGROUND OF THE INVENTION

1. Field of the Invention

This invention involves, in general, the field of medical equipment. More particularly it concerns an optical feedback device for laser surgical devices that controls the amount of white light produced during the burning of biological tissue residues adhering to the laser fiber, while simultaneously discriminating against background white light.

2. Information Disclosure Statement

Contact/non-contact surgical techniques employing laser radiation have been in development for several years. Laser beam manipulator devices have been employed as surgical scalpels as illustrated in, for example, U.S. Pat. No. 3,865,113 of Sharon et al; European Patent Application Serial No. 75912 of Hitachi Ltd. and West German Patent No. 3105297 of Asaki Kogaku Kogyo. Laser devices can also be used to effect blood coagulation or to cauterize as shown by, for example, U.S. Patent No. 3,487,835 of Koester et al.

While it is necessary to precisely control the amount of laser radiation delivered to biological tissue in photo-surgical procedures, it is also necessary to control the rate of burning residue tissue of the optical fiber tip to prevent the fiber from going into a thermal runaway condition.

There currently exists a laser system in which a white light optical feedback controller can control the rate of burning residue tissue by reducing the laser's output power.

While this prior preferred embodiment has proven very effective, it has one serious drawback. In most applications, it is mandatory to have background illumination present (i.e. laprascopic and gynecological applications). Since many of the background illuminators produce similar wavelengths, such as those produced by the burning of the white light tissues, the optical feedback fails to discriminate. Consequently, the lasers erroneously reduces power as if to compensate for burning fiber.

This invention, in addition to this earlier disclosed feedback peripheral, provides discrimination between white light produced by burning of biological tissue and white light from background illumination. This facilitates the use of white light control feedback in the presence of white light background illumination.

SUMMARY OF THE INVENTION

The present invention is directed to an independent optical controller that can enable an optical surgical therapeutic source, such as a laser, to alternate contact for cutting and non contact for coagulation of biological tissue by means of an optically guided laser radiation device, such as an optical fiber, in the presence on interfering background radiation. The present invention is directed to control of the output laser device by altering that output power based on feedback from white light which is produced during the burning of biological tissue by the laser. The present invention is an improved feedback type laser system in that it discriminates between white light created by the burning of biological tissue and white light created by background illumination.

BRIEF DESCRIPTION OF THE DRAWINGS

The present invention is more fully understood when the specification herein is taken in conjunction with the drawings appended hereto, wherein.

DETAILED DESCRIPTION OF THE PRESENT INVENTION

An improved configuration for an optical (laser) surgical instrument with white light feedback control has now been found. This configuration, which is an improved device over prior art white light feedback devices, includes means by which to prevent white light background radiation from interfering with laser operation while discriminating between generated white light and background white light.

It is, therefore, an object of this invention to provide instrument or laser accessory for alternate contact cutting and non-contact coagulation of biological tissue endoscopically or non-endoscopically by means of fiber-optically guided irradiation of a laser which provides methods for simultaneously controlling the white light produced by burning of biological tissues while discriminating against background white light. This discrimination will allow for the presence of background illumination during operation of a laser equipped with a white light feedback system to perform with a normal predictable power output. In further preferred aspects, this invention will allow the surgeon to perform laser surgery with more predictable results yielding a safer and faster procedure, and eliminating certain forms of undesired or runaway burning.

First, in order to further understand the details of this invention, a brief detailed description of the prior art preferred embodiment is discussed.

Figure 1:
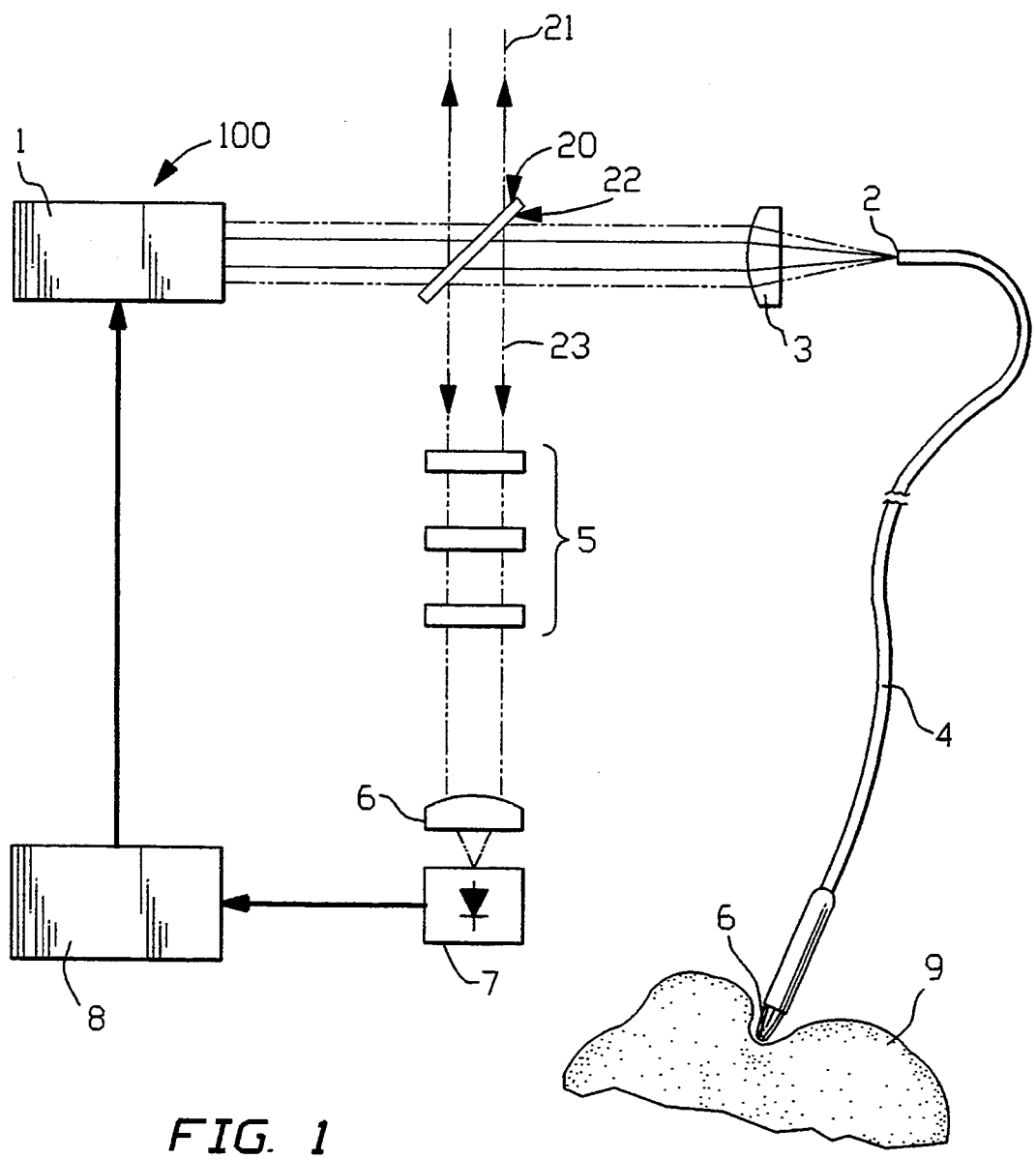
FIG. 1 shows a diagrammatic representation of a prior art laser device and optical controller.

Referring to FIG. 1, the prior preferred embodiment, a medical laser system 100 with white light feedback is illustrated including an exemplary peripheral surgical device 4. Radiation is coupled from the medical laser 1 into the proximal end 2 of the exemplary peripheral surgical device 4, such as an optical fiber, after first passing unimpaired through an optical band pass beam splitter 20 (except for selected light, e.g., white light 21 reflected away) and focused through a lens system 3.

Any light having wavelengths between 0.3 and 0.9 microns, termed "white light", incident form the proximal fiber end 16 toward the beam splitter 20 will be reflected 22, on surface 22 as beam 23, filtered through filter 5 and focused by condensing lens onto a photodetector circuit. The photo-detector circuit 7 creates a proportional electrical signal and sends it to a controller 8 where it is compared with a preset value. If this signal exceeds a preset value, then the controller 8 will indirectly reduce the laser output by sending a signal to the laser to reduce the power supply drive that ultimately reduces the output power.

Figure 2:
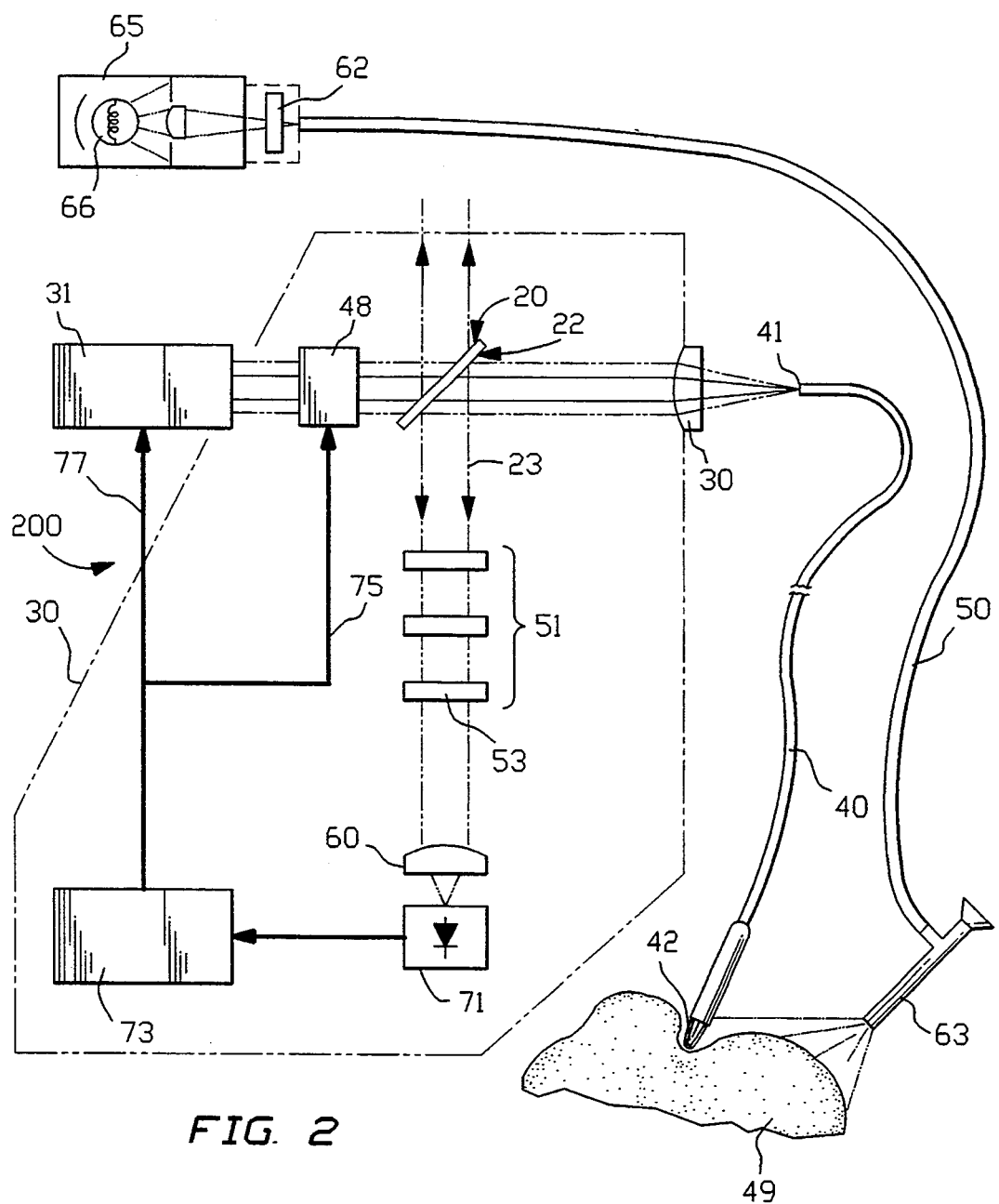
FIG. 2 shows a diagrammatic representation of a present invention laser device and optical controller.

Now referring to FIG. 2, a light feedback control system 200, of the present invention using optical background discrimination 30 (enclosed, dotted lines) is illustrated. It includes an optical therapeutic source, such as a laser 31, an exemplary background illumination source 65, and an exemplary peripheral surgical device 40. The background illumination source 65 includes light unit 66 with concentration and filtering as desired, eg. filter 62, light tube guide 50 and sight tube 63. The light itself could be Xenon or other selected band or even a filtered portion of a selected light band.

Radiation is coupled from the medical laser 31 into the proximal end 41 of the exemplary peripheral surgical device 40, such as an optical fiber with operational end 42, after first passing unimpaired through an optical modulator 48, optical band pass beam splitter 20 and focused (through a condensing lens system) 30. The radiation then exits fiber operational end 42 at tissue 49 for desired surgical procedures. Any light having wavelengths within the chosen reflection bands 22 (eg., 0.3 to 0.9 μm) incident from the fiber end 41 toward the beam splitter will be reflected as light 23, filtered through filter 51 and focused through lens 60 onto a photo-detector circuit 71. The photo-detector circuit 71 creates a proportional electrical signal and sends it to a controller 73 where it is compared with a preset minimum acceptable value. If this signal exceeds the preset value, then the controller 73 (e.g., microprocessor) will directly reduce the laser output by modulating the optical modulator 48 via line 75. If desired, the laser output could alternatively be indirectly controlled by controlling the power supply of the laser 31 via line 77. In this case the optical modulator 48 would not be required. However, as an add on feature for an existing laser device, the optical modulator is preferred. The optical discrimination of white light produced burning residual tissue on a fiber end and background illumination is centered on producing a sufficient signal to noise ratio. Note the prior art embodiment of FIG. 1 did use filtering to enhance the optical signal to noise ratios, but unfortunately did not address the optical noise, such as bright background illumination, that had similar optical wavelengths to their detection signal. Whereas, the filter system 51 and/or the complementary filter system 62, instead of filtering out just wavelengths outside the desired optical detection band, also filters optical bands within noise and detection signal spectrum to create a superior signal to noise ratio.

For example, assume the illumination source and the detection signal were both white light bands from 0.3 to 0.9 microns with equal irradiance. In this condition, optical discrimination would be extremely difficult, if not impossible. However, suppose that filter 62 was limited to a narrow band of a selected light color, e.g., green, which still provided enough background illumination to perform a given surgical procedure. Filter unit 53 could be designed to pass all the desired 0.3 to 0.9 microns except for a narrow, green illumination band. This, of course, would greatly increase the signal to noise band and provide for discrimination against background illumination.

It would further be desirous for both the filter and the detector systems to be removable for enhancing signal to noise for various other detection wavelengths and illumination wavelengths.

Also, it would be to be able to verify that normal background illumination is maintained. This could be foreseen by an optional indicator from the controller to indicate during standby, that background illumination is sufficient enough to begin undesirable erroneous regulation of the output power. Standby would sometimes require the therapeutic light source (the laser) to be off.

A second optional indicator could also be useful to show the amount of output regulation.

Also, considerations should be given to different optical detectors with respective responses when trying to achieve a superior signal to noise ratio with respect to a given optical background, signal and therapeutic sources.

Figure 3:
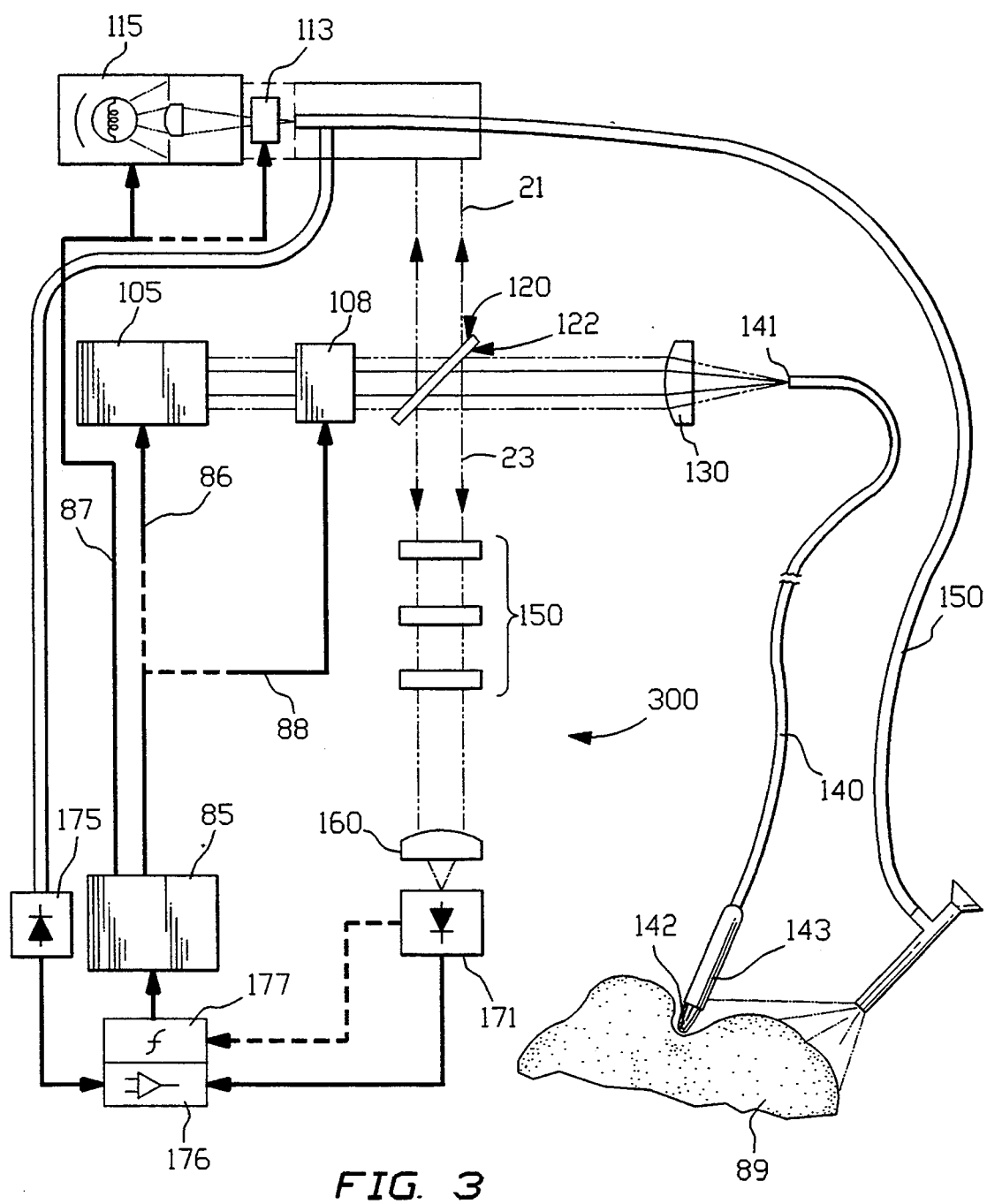
FIG. 3 shows a diagrammatic representation of an alternative present invention laser device and optical controller embodiment.

Finally, referring to FIG. 3, an alternative multiple optical feedback control system 300 using electronic background discrimination is illustrated, including an optical therapeutic source 105, such as a laser, an exemplary background illumination source 115, and an exemplary peripheral surgical device 140.

Similarly as in FIG. 1 of the prior art embodiment, radiation is coupled from the medical laser 105 into the proximal end 141 of the exemplary peripheral surgical device 140, such as an optical fiber, after first passing unimpaired through an optical modulator 108, optical band pass beam splitter 120, and focused through a lens system 130. The radiation then passes through device 140 and exits at fiber operational end 142 at tissue 89.

Any light having wavelengths 122 between 0.3 and 0.9 microns, termed "white light", incident from the fiber end 141 toward the beam splitter 120 will be reflected as light 123, filtered through filter 150 and focused through lens 160 onto a photo-detector circuit 171. The photodetector circuit 171 creates a proportional electrical signal and sends it either directly to a (digital or analog) frequency filter network 176 or to a comparative filter network 177. Note these filter networks as well as others could be used in combination or separately. As an example of frequency filter, suppose electrical characteristics from the background illumination 115 contained an A.C. component. Once detected, this attribute could be used for rejecting that background white light produced from the A.C. source and thus improving the signal to noise to enable discrimination. Comparative filtering could require a sample of the background source through photo-detector 175 to allow this signal to be subtracted from additive signal created at detector 171. Again, subtracting out the background signal could increase the signal to noise ratio. The signal from either or both of networks 176 and 177 are sent to controller 85 which then sends a signal via line 86 directly to laser 105 or to optical modulator 108 via line 88 to regulate laser output once a predetermined threshold level of pyrolytic light is recognized, also controller 85 via line 87 may optionally control background illumination source 115 and/or source 115's modulator comparisons, and/or to create baseline data.

A possible third alternative could be the (digital or analog) modulation of the background illumination and/or the therapeutic source. This type of modulation is useful for creating hetrodyne techniques such as those used with lock-in amplifiers to improve signal to noise ratios.

Obviously, numerous modifications and variations of the present invention are possible in light of the above teachings. It is therefore understood that within the scope of the appended claims, the invention may be practiced otherwise than as specifically described herein.

What is claimed is:

1. A method of controlling a surgical laser instrument comprising the steps of:
   generating a laser beam;
   guiding said laser beam onto biological tissue;

detecting radiation emitted by pyrolytic glowing of at least partially carbonized biological tissue and by background illumination wherein said background illumination is intentionally created so as to be only within a very narrow spectral band relative to the spectral band radiation emitted by pyrolytic glowing of biological tissue;

separating radiation emitted by pyrolytic glowing from radiation emitted by background illumination; and, controlling the intensity of said laser beam in response to the intensity of radiation detected from the pyrolytic glowing of said biological tissue while excluding radiation detected from background illumination.

2. The method according to claim 1 wherein said step of guiding laser beam onto biological tissue is performed by means of a light guide.

3. The method according to claim 2 wherein in said controlling step the intensity of said laser beam is controlled such that the intensity of the radiation detected in said detecting step does not exceed a level that corresponds to a predetermined destruction threshold of the light guide.

4. The method according to claim 1 wherein said pyrolytic glowing radiation is within the spectral region between 0.3 and 0.9 $\mu$m.

* * * * *